United States Patent
Ichioka et al.

(10) Patent No.: US 9,173,639 B2
(45) Date of Patent: Nov. 3, 2015

(54) DIAGNOSTIC IMAGING APPARATUS, DIAGNOSTIC ULTRASONIC APPARATUS, AND MEDICAL IMAGE DISPLAYING APPARATUS

(75) Inventors: Kenichi Ichioka, Nasushiobara (JP);
Kuramitsu Nishihara, Otawara (JP);
Muneki Kataguchi, Nasushiobara (JP)

(73) Assignees: Kabushiki Kaisha Toshiba, Tokyo (JP);
Toshiba Medical Systems Corporation, Otawara-shi (JP)

( * ) Notice: Subject to any disclaimer, the term of this patent is extended or adjusted under 35 U.S.C. 154(b) by 288 days.

(21) Appl. No.: 13/107,249

(22) Filed: May 13, 2011

(65) Prior Publication Data
US 2011/0282206 A1    Nov. 17, 2011

(30) Foreign Application Priority Data
May 14, 2010    (JP) .................................. 2010-112293
Apr. 1, 2011    (JP) .................................. 2011-082083

(51) Int. Cl.
*A61B 8/00*    (2006.01)
*A61B 6/00*    (2006.01)

(52) U.S. Cl.
CPC ................. *A61B 8/463* (2013.01); *A61B 8/465* (2013.01); *A61B 6/463* (2013.01); *A61B 6/465* (2013.01)

(58) Field of Classification Search
CPC ........ A61B 6/463; A61B 6/465; A61B 8/463; A61B 8/465
USPC .......... 600/407, 437–475; 715/700, 716–722, 715/764–807, 810–862
See application file for complete search history.

(56) References Cited

U.S. PATENT DOCUMENTS

| | | | |
|---|---|---|---|
| 6,938,216 B1 * | 8/2005 | Ishisaki .......................... | 715/817 |
| 2006/0116578 A1 * | 6/2006 | Grunwald et al. ............. | 600/440 |
| 2009/0043195 A1 * | 2/2009 | Poland ........................... | 600/437 |

FOREIGN PATENT DOCUMENTS

| | | |
|---|---|---|
| CN | 101299179 A | 11/2008 |
| JP | 2000-254127 A | 9/2000 |
| JP | 2008-29468 A | 2/2008 |
| JP | 2008-515583 A | 5/2008 |
| JP | 2008-245789 A | 10/2008 |
| JP | 2009-131419 | 6/2009 |
| WO | WO 2009/031443 A1 | 3/2009 |

OTHER PUBLICATIONS

Combined Office Action and Search Report issued on Jan. 12, 2015 in Chinese Patent Application No. 201110126555.7 with English translation of category of cited documents.
Japanese Office Action issue Mar. 3, 2015 in Patent Application No. 2011-082083 (without English Translation).

* cited by examiner

*Primary Examiner* — Mark Remaly
(74) *Attorney, Agent, or Firm* — Oblon, McClelland, Maier & Neustadt, L.L.P.

(57) ABSTRACT

The diagnostic imaging apparatus according to the present embodiments includes a display unit, an input unit, and a display control unit. The display unit includes a display area in which a medical image and a menu in relation to the medical image are displayed. The input unit receives input to the display area. The display control unit displays different menus in the display area in accordance with the input received by the input unit.

19 Claims, 10 Drawing Sheets

FIG.3

| PRESET INFOR-MATION | AREA INFORMATION | | | MENU INFORMATION | | | | | | |
|---|---|---|---|---|---|---|---|---|---|---|
| | | | | LIVE DISPLAY | | | FREEZE DISPLAY | | | |
| | AREA | POSITION | SIZE | 2D IMAGING | COLOR IMAGING | DOPPLER IMAGING | 2D IMAGING | COLOR IMAGING | DOPPLER IMAGING | |
| ABDOMEN | 1 | 10, 10 | 495, 120 | PATIENT INFORMATION | ... | ... | MEASURE-MENT 1 | ... | ... | |
| | 2 | 10, 140 | 170, 480 | IMAGE QUALITY PARAMETER | ... | ... | ANNOTA-TION | ... | ... | |
| | 3 | 515, 10 | 495, 120 | PRESET | ... | ... | MEASURE-MENT 2 | ... | ... | |
| | 4 | 840, 140 | 170, 480 | PROBE SELECTION | ... | ... | BODY MARK | ... | ... | |
| | 5 | 10, 630 | 1000, 120 | IMAGE VIEWING | ... | ... | IMAGE VIEWING | ... | ... | |
| KIDNEY | 1 | ... | ... | ... | ... | ... | ... | ... | ... | |
| | 2 | ... | ... | ... | ... | ... | ... | ... | ... | |
| | 3 | ... | ... | ... | ... | ... | ... | ... | ... | |
| THYROID GLAND | 1 | ... | ... | ... | ... | ... | ... | ... | ... | |
| | 2 | ... | ... | ... | ... | ... | ... | ... | ... | |
| | 3 | ... | ... | ... | ... | ... | ... | ... | ... | |
| | ... | ... | ... | ... | ... | ... | ... | ... | ... | |

DIAGNOSTIC IMAGING APPARATUS, DIAGNOSTIC ULTRASONIC APPARATUS, AND MEDICAL IMAGE DISPLAYING APPARATUS

CROSS-REFERENCE TO RELATED APPLICATIONS

This application is based upon and claims the benefit of priority from Japanese Patent Application No. 2010-112293, filed on May 14, 2010; and Japanese Patent Application No. 2011-82083, filed on Apr. 1, 2011, the entire contents of all of which are incorporated herein by reference.

FIELD

Embodiments described herein relate generally to a diagnostic imaging apparatus, a diagnostic ultrasonic apparatus, and a medical image displaying apparatus.

BACKGROUND

A diagnostic ultrasonic apparatus generates an ultrasonic image from a reflection wave signal that is obtained by scanning a subject with an ultrasonic probe. Some of the diagnostic ultrasonic apparatus are provided with a touch panel to display an ultrasonic image and also to receive various operations from an operator. For such diagnostic ultrasonic apparatus incorporating a touch panel, a conventional technology has been known that displays graphics such as switches, icons, and tabs on the monitor of the touch panel, receives operations with respect to these graphics, and thereby displays various menus for an ultrasonic image.

With such a conventional technology, however, if graphics such as switches, icons, and tabs are constantly displayed on the monitor, these graphics reduce the display area of an ultrasonic image. Thus, the display area is not always effectively used during examination of a medical image such as an ultrasonic image according to the conventional technology.

BRIEF DESCRIPTION OF THE DRAWINGS

FIG. 3 is a diagram for showing an example of setting information stored in a setting information storage unit according to the first embodiment;

DETAILED DESCRIPTION

A diagnostic imaging apparatus, a diagnostic ultrasonic apparatus, and a medical image displaying apparatus according to the present embodiments are explained in detail below with reference to the attached drawings.

The diagnostic imaging apparatus, the diagnostic ultrasonic apparatus, and the medical image displaying apparatus according to the present embodiment include a display unit, an input unit, and a display control unit. The display unit is provided with a display area in which a medical image is displayed. The input unit receives inputs with respect to the display area. The display control unit displays different menus in the display area in accordance with the input received by the input unit.

Figure 1:
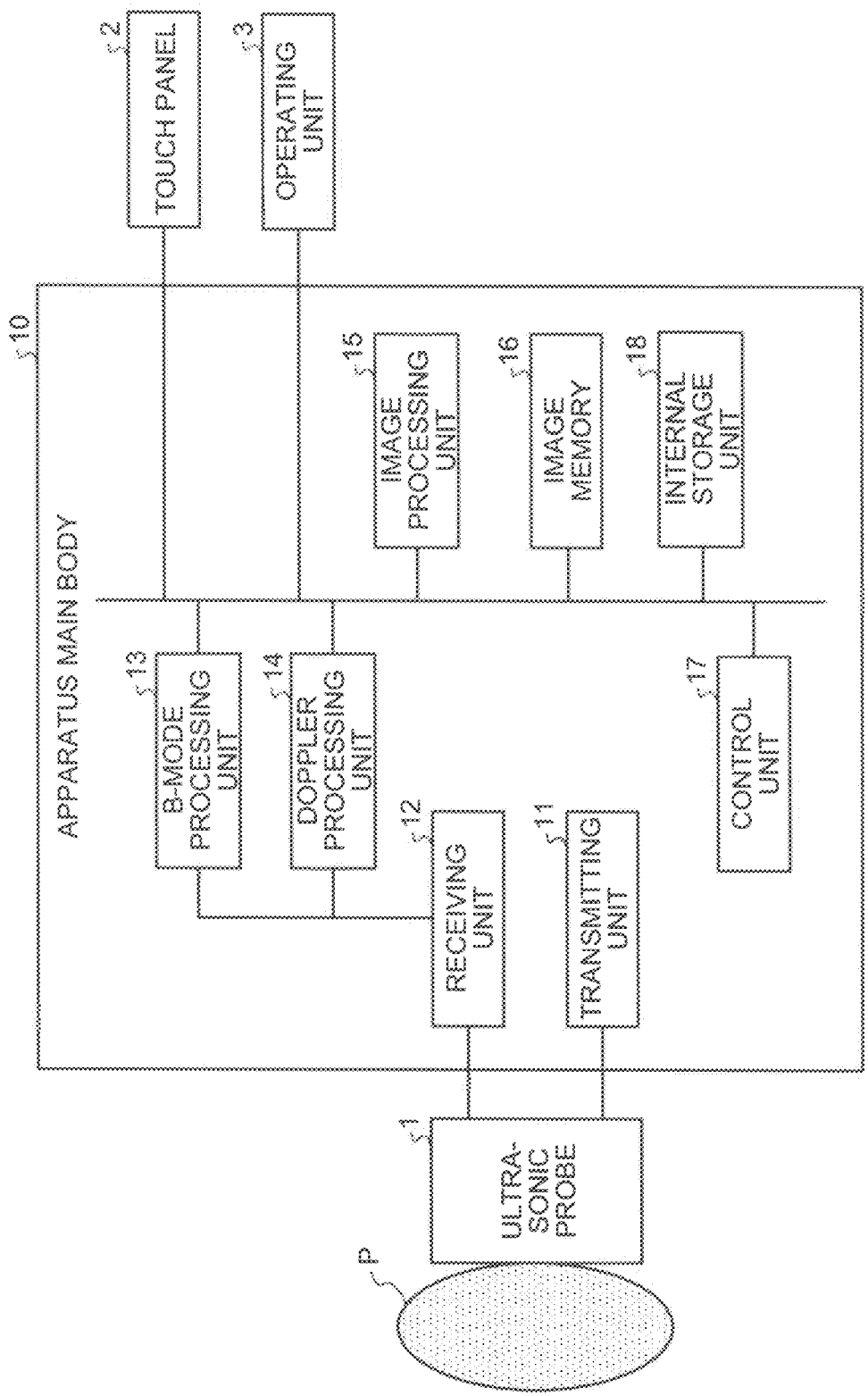
FIG. 1 is a block diagram for showing the structure of a diagnostic ultrasonic apparatus according to the first embodiment.

First, the structure of the diagnostic ultrasonic apparatus is explained as the first embodiment. FIG. 1 is a block diagram for showing the structure of the diagnostic ultrasonic apparatus according to the first embodiment. As illustrated in FIG. 1, the diagnostic ultrasonic apparatus according to the first embodiment includes an ultrasonic probe 1, a touch panel 2, an operating unit 3, and an apparatus main body 10.

The ultrasonic probe 1 is provided with multiple piezoelectric transducers. Each of the piezoelectric transducers generates ultrasonic waves in accordance with a drive signal supplied from a later-described transmitting unit 11 of the apparatus main body 10, and moreover, it receives waves reflected from a subject P and converts it to an electronic signal. The ultrasonic probe 1 is also provided with a matching layer on the piezoelectric transducers, a backing material that prevents ultrasonic waves from propagating backwards from the piezoelectric transducers, and the like.

When the ultrasonic probe 1 transmits an ultrasonic wave to the subject P, the transmitted ultrasonic wave is reflected sequentially from the surfaces of the body tissue of the subject P with acoustic impedance discontinuities, and the multiple piezoelectric transducers of the ultrasonic probe 1 receive it as a reflection wave signal. The amplitude of the reflection wave signal depends on a difference in the acoustic impedances of the discontinuous surface from which the ultrasonic wave is reflected. When the transmitted ultrasonic pulses are reflected from the flowing bloodstream or the surfaces of the cardiac wall or the like, the frequency of the reflection wave signal is shifted due to the Doppler effect, in accordance with the velocity component in the ultrasonic wave transmission direction in the moving body.

The touch panel 2 displays an ultrasonic image generated by the apparatus main body 10, and also receives various operations from the operator of the diagnostic ultrasonic apparatus. This touch panel 2 will be discussed in detail later.

The operating unit 3 includes input devices such as a mouse, a keyboard, buttons, panel switches, and a trackball, and receives various setting requests from the operator by way of the input devices. Then, the operating unit 3 transmits the received setting requests to the apparatus main body 10.

The apparatus main body 10 generates an ultrasonic image in accordance with the reflection wave signal received by the ultrasonic probe 1. This apparatus main body 10 includes a transmitting unit 11, a receiving unit 12, a B-mode processing unit 13, a Doppler processing unit 14, an image processing unit 15, an image memory 16, a control unit 17, and an internal storage unit 18.

The transmitting unit 11 includes a trigger generating circuit, a delaying circuit, a pulsar circuit, and the like, and supplies a drive signal to the ultrasonic probe 1. The pulsar circuit repeatedly generates rate pulses at a certain rate frequency to create a transmission ultrasonic wave. Furthermore, the delaying circuit gives a delay time for each piezoelectric transducer to each rate pulse generated by the pulsar circuit so that it is used to gather the ultrasonic wave generated by the ultrasonic probe 1 into a beam and determine the transmission directionality. Furthermore, the trigger generating circuit supplies a drive signal to the ultrasonic probe 1 at a timing based on the rate pulse.

The receiving unit 12 includes an amplifying circuit, an A/D converter, an adder, and the like, and performs various processing onto the reflection wave signal received by the ultrasonic probe 1 to generate reflection wave data. The amplifying circuit performs gain correction by amplifying the reflection wave signal; the A/D converter performs A/D conversion onto the gain-corrected reflection wave signal and gives it a delay time necessary to determine the reception directionality; the adder performs an addition onto the reflection wave signal that is processed by the A/D converter; and thereby the reflection wave data is generated. In the addition performed by the adder, the reflection component of the direction corresponding to the reception directionality of the reflection wave signal is enhanced.

In this manner, the transmitting unit 11 and the receiving unit 12 control the transmission directionality and the reception directionality during the transmission/reception of the ultrasonic wave.

The B-mode processing unit 13 receives the reflection wave data from the receiving unit 12 and performs logarithmic amplification and envelop detection to generate data (B-mode data) that represents the intensity of the signal by the level of brightness.

The Doppler processing unit 14 performs frequency analysis on the velocity information of the reflection wave data received from the receiving unit 12, extracts echo components of the bloodstream, tissue, and contrast agent by use of the Doppler effect, and thereby generates data (Doppler data) from the extracted multipoint information of the moving bodies such as the average speed, dispersion, and power.

The image processing unit 15 generates an ultrasonic image from the B-mode data generated by the B-mode processing unit 13 and the Doppler data generated by the Doppler processing unit 14. For example, the image processing unit 15 generates a B-mode image from the B-mode data and a Doppler image from the Doppler data.

The image memory 16 stores therein the ultrasonic image generated by the image processing unit 15.

The control unit 17 controls the entire process of the diagnostic ultrasonic apparatus. For example, the control unit 17 controls the transmitting unit 11, the receiving unit 12, the B-mode processing unit 13, the Doppler processing unit 14, and the image processing unit 15, based on various setting requests input by the operator by way of the operating unit 3 and various controlling programs and various types of setting information that are read from the internal storage unit 18. In addition, the control unit 17 displays the ultrasonic image stored in the image memory 16 on the touch panel 2. This control unit will be explained in detail later.

The internal storage unit 18 stores therein controlling programs that are used for various processes such as ultrasonic wave transmission/reception, image processing, and display processing, and various kinds of data such as diagnostic information (e.g., patient IDs and doctor's remarks), diagnostic protocols, and setting information. Moreover, the internal storage unit 18 is used, if necessary, also for storage of images stored in the image memory 16. The data stored in the internal storage unit 18 may be transferred to an external peripheral device by way of a not-shown interface circuit. The internal storage unit 18 will be discussed in detail later.

The structure of the diagnostic ultrasonic apparatus according to the first embodiment has been explained. With such a structure, the touch panel 2 of the diagnostic ultrasonic apparatus according to the first embodiment has a display area in which an ultrasonic image is displayed, and receives a position input operation to input any position in the display area. When the position input operation is received, the control unit 17 displays a menu in relation to the ultrasonic image in the display area of the touch panel 2.

In other words, the diagnostic ultrasonic apparatus according to the first embodiment displays an ultrasonic image in the entire display area of the touch panel 2 during the examination of the ultrasonic image, and, only when the operator desires, it displays a necessary menu in the display area. Thus, according to the first embodiment, the display area of the monitor can be effectively used when an ultrasonic image is examined.

Figure 2:
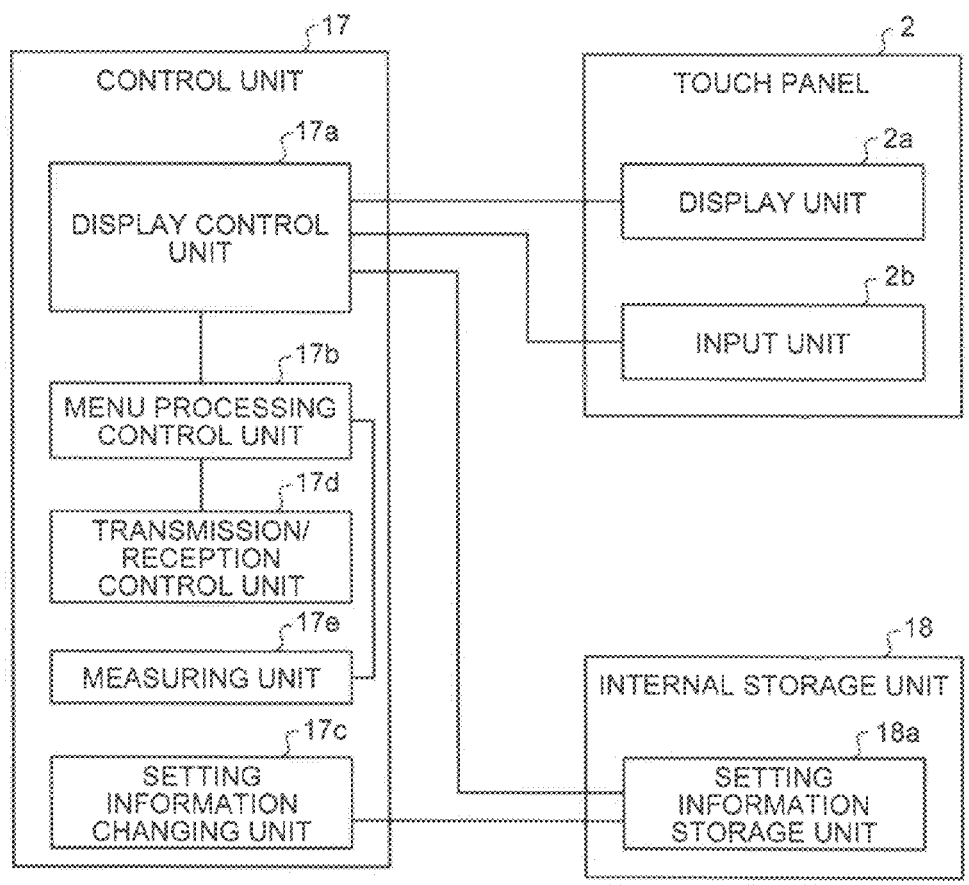
FIG. 2 is a functional block diagram for showing the structure of the diagnostic ultrasonic apparatus according to the first embodiment.

Next, the detailed structure of the diagnostic ultrasonic apparatus according to the first embodiment is discussed. FIG. 2 is a functional block diagram for showing the detailed structure of the diagnostic ultrasonic apparatus according to the first embodiment. In FIG. 2, the touch panel 2, the control unit 17, and the internal storage unit 18 illustrated in FIG. 1 are presented. Here, the touch panel 2, the control unit 17, and the internal storage unit 18 are explained in detail with reference to FIG. 2.

The touch panel 2 includes a display unit 2a and an input unit 2b.

The display unit 2a includes a display area in which an ultrasonic image is displayed. For example, the display unit 2a displays an ultrasonic image and various menus in relation to the ultrasonic image, under the control of the later-described display control unit 17a. The display unit 2a may be a liquid crystal monitor.

The input unit 2b receives the position input operation that is to input a position in the display area of the display unit 2a. As the position input operation, for example, the input unit 2b receives from the operator an operation of touching any position in the display area of the display unit 2a. When the position in the display area is touched by the operator, the input unit 2b sends the screen position information that indicates the touched position to the later-described display control unit 17a.

The internal storage unit 18 includes a setting information storage unit 18a. This internal storage unit 18 may be a hard disk drive or a non-volatile semiconductor memory.

The setting information storage unit 18a stores therein setting information in which the area information and the menu information are brought into correspondence. FIG. 3 is a diagram for showing an example of the setting information stored in the setting information storage unit 18a according to the first embodiment. As illustrated in FIG. 3, for example, the setting information storage unit 18a stores therein information in which the preset information, the area information, and the menu information are brought into correspondence, as the setting information.

The preset information indicates the diagnosis target site. For example, "abdomen", "kidney", or "thyroid gland" may be entered in the preset information. When an ultrasonic image is taken with the diagnostic ultrasonic apparatus according to the first embodiment, the operator selects a diagnosis target site from among the sites entered in the preset information.

The area information indicates an area arranged in the display area of the display unit 2a. For example, the area information includes three items, "area", "position", and "size". A number is assigned to each area to uniquely identify the individual areas arranged in the display area among the same preset information. For the positions, area position information is entered to indicate the positions of the areas arranged in the display area. For the sizes, area size information is entered to indicate the sizes of the areas arranged in the display area.

The menu information indicates types of menus in relation to the ultrasonic image. According to the first embodiment, the menu information is determined for different display modes and different imaging modes. For example, information on menus for live display and for freeze display is determined as the menu information. Here, the live display menu is used during the live display of an ultrasonic image. Meanwhile, the freeze display menu is used during the freeze display of the ultrasonic image. In addition, the menu information for these display modes is determined for each imaging mode. For example, information regarding 2D imaging (imaging of a two-dimensional image), color imaging, and Doppler imaging is determined for the menu information of each display mode.

Then, information indicating various types of menus is determined in the menu information for each display mode and each imaging mode. For example, "patient information", "image quality parameter", "preset", "probe selection", "image viewing", "measurement 1", "annotation", "measurement 2", "body mark", and the like are set in each item of the menu information. The menus corresponding to such menu information will be discussed in detail later.

With the setting information storage unit 18a storing therein the setting information in which the area information and the menu information are brought into association with each other, one area or more are determined in the display area of the display unit 2a. Furthermore, with the setting information storage unit 18a storing therein the menus in correspondence with the display mode and the imaging mode for each area determined in the display area, a menu that is to be displayed in response to the designation of an area can be defined.

In FIG. 2, the control unit 17 includes the display control unit 17a, a menu processing control unit 17b, a setting information changing unit 17c, a transmission/reception control unit 17d, and a measuring unit 17e.

The display control unit 17a displays the ultrasonic image, various menus in relation to the ultrasonic image, and the like onto the display unit 2a. For example, the display control unit 17a displays the ultrasonic image generated by the apparatus main body 10 live on the display unit 2a. Furthermore, for example, when the operator sends an instruction of freeze display, the display control unit 17a freezes (displays a still image of) the ultrasonic image generated by the apparatus main body 10 on the display unit 2a.

Here, for example, the display control unit 17a may display a transmission/reception menu for receiving termination or start of the ultrasonic wave transmission/reception in a display area 20, in accordance with the input received by the input unit 2b. If the operator instructs termination of the ultrasonic wave transmission/reception, the last ultrasonic image generated by the apparatus main body 10 is freeze-displayed on the display unit 2a. Moreover, when the operator instructs the start of the ultrasonic wave transmission/reception, the ultrasonic image generated by the apparatus main body 10 is displayed live.

In addition, for example, when the input unit 2b receives a position input operation, the display control unit 17a displays a menu in relation to the ultrasonic image in the display area of the display unit 2a. The display control unit 17a displays different menus in the display area in accordance with the input received by the input unit 2b. More specifically, the display control unit 17a displays, in the display area of the display unit 2a, a menu that is brought into correspondence with the area including the position input through the position input operation, based on the setting information stored in the setting information storage unit 18a.

More specifically, the display control unit 17a displays various menus, in accordance with the diagnosis target site that is selected by the operator from the preset information at the imaging of the ultrasonic image. In addition, the display control unit 17a determines which of the live display menu and the freeze display menu is to be displayed, in accordance with the ultrasonic image that is live-displayed or freeze-displayed. Furthermore, the display control unit 17a displays a menu in accordance with the imaging mode.

Figure 4:
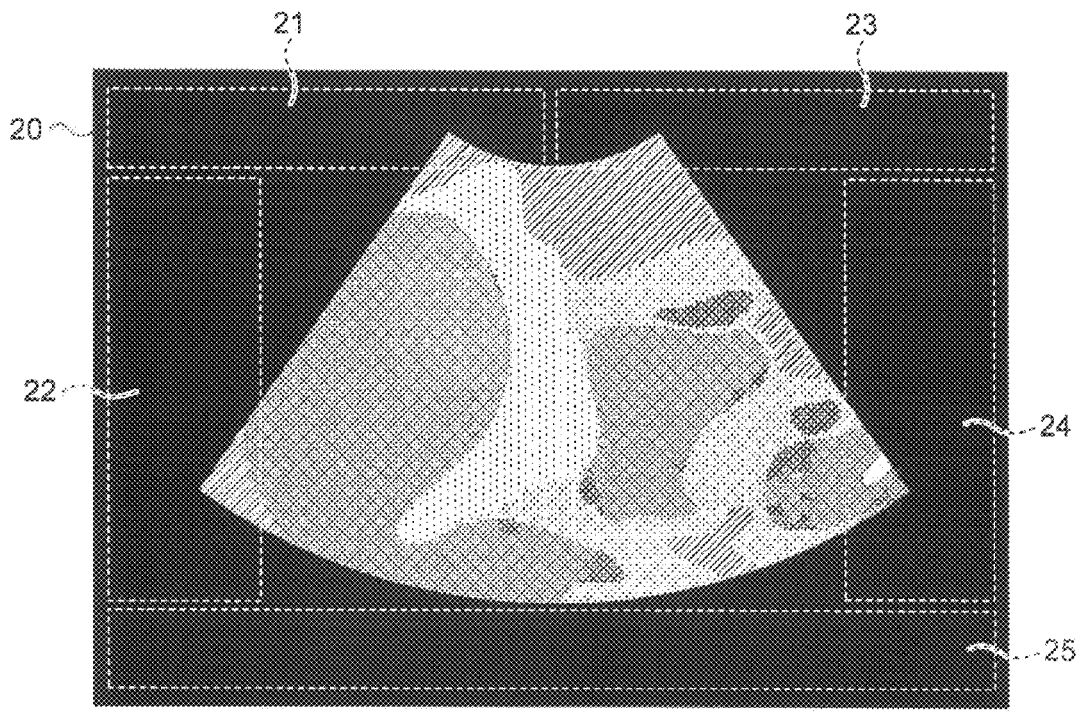
FIGS. 4 to 10 are diagrams for showing menus that are displayed by a display control unit according to the first embodiment.

FIGS. 4 to 10 are diagrams for explaining menus that are displayed by the display control unit 17a according to the first embodiment. It is assumed here that the setting information storage unit 18a stores therein the setting information indicated in FIG. 3. Furthermore, it is assumed that the abdomen is selected as the diagnosis target site, the live display is selected as the display mode, and 2D imaging is selected as the imaging mode. In this situation, as indicated in FIG. 4, five areas, 21 to 25, are arranged in the display area 20 of the display unit 2a.

In FIG. 4, an area 21 corresponds to the data in which the preset information shows "abdomen" and the area of the area information shows "1" according to the setting information of FIG. 3. Further, an area 22 corresponds to the data in which the preset information shows "abdomen" and the area of the area information shows "2". In addition, an area 23 corresponds to the data in which the preset information shows "abdomen" and the area of the area information shows "3". An area 24 corresponds to the data in which the preset information shows "abdomen" and the area of the area information shows "4". An area 25 corresponds to the data in which the preset information shows "abdomen" and the area of the area information shows "5". For convenience of explanation, the areas 21 to 25 are indicated in broken lines in FIG. 4, but no broken lines are actually displayed in the display area 20.

When the input unit 2b receives the operation of touching any position in the display area 20, the display control unit 17a receives the screen position information that indicates the touched position from the input unit 2b. Then, the display control unit 17a identifies the area that includes the position indicated by the received screen position information, based on the area position information and the area size information for each area that are included in the setting information stored in the setting information storage unit 18a, and displays the menu that corresponds to the identified area in the display area 20.

Figure 5:
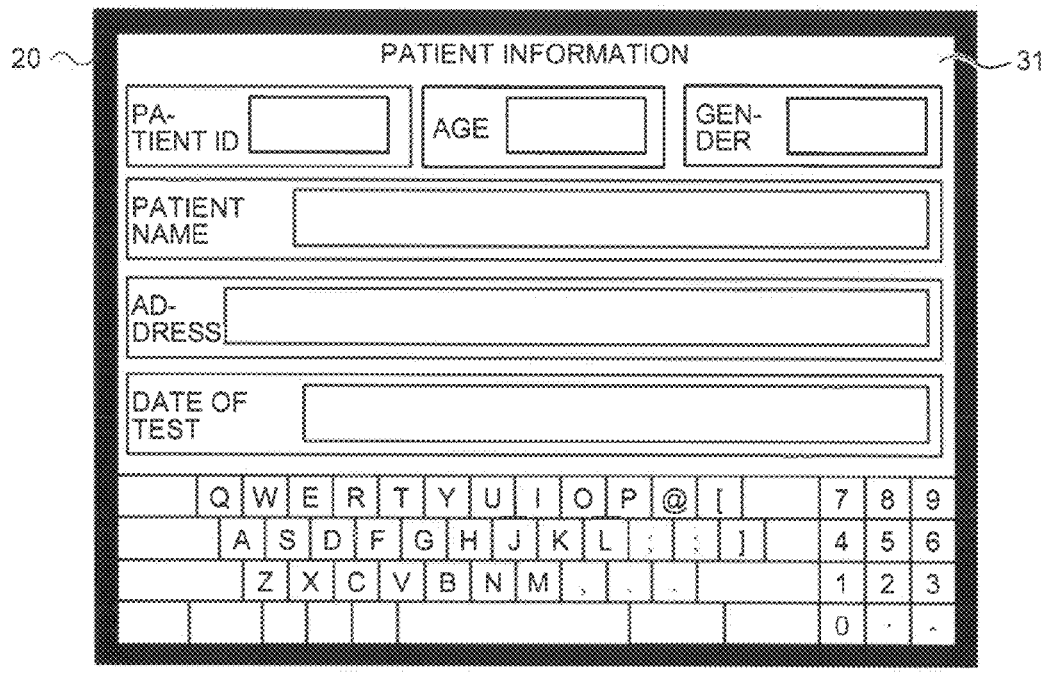

It is assumed, for example, that the operation of touching the area 21 is received by the input unit 2b. Here, according to the setting information of FIG. 3, the data corresponding to the area 21 includes "patient information" in the menu information for the live display of the 2D imaging. Thus, for this case, the display control unit 17a displays a patient information menu 31 in the display area 20, as indicated in FIG. 5. The patient information menu 31 is used by the operator to input information on the diagnosis target patient, such as a patient ID that uniquely identifies the patient and the age, gender, and name of the patient.

Figure 6:
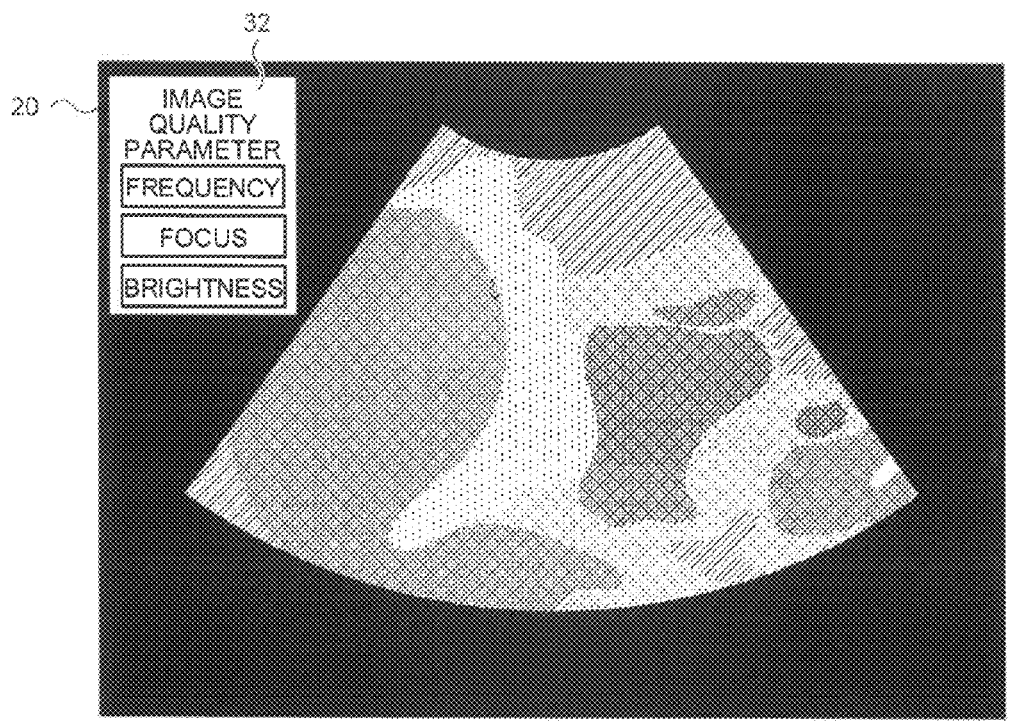

Furthermore, for example, the input unit 2b receives the operation of touching the area 22. Here, according to the setting information of FIG. 3, the data corresponding to the area 22 includes "image quality parameter" in the menu information for live display of 2D imaging. Thus, for this case, the display control unit 17a displays an image quality parameter menu 32 in the display area 20, as illustrated in FIG. 6. The image quality parameter menu 32 is used by the operator to input information on the quality of the ultrasonic image, such as the frequency of the ultrasonic wave generated by the ultrasonic probe 1, the focus of the ultrasonic wave, and the brightness of the ultrasonic image.

Figure 7:
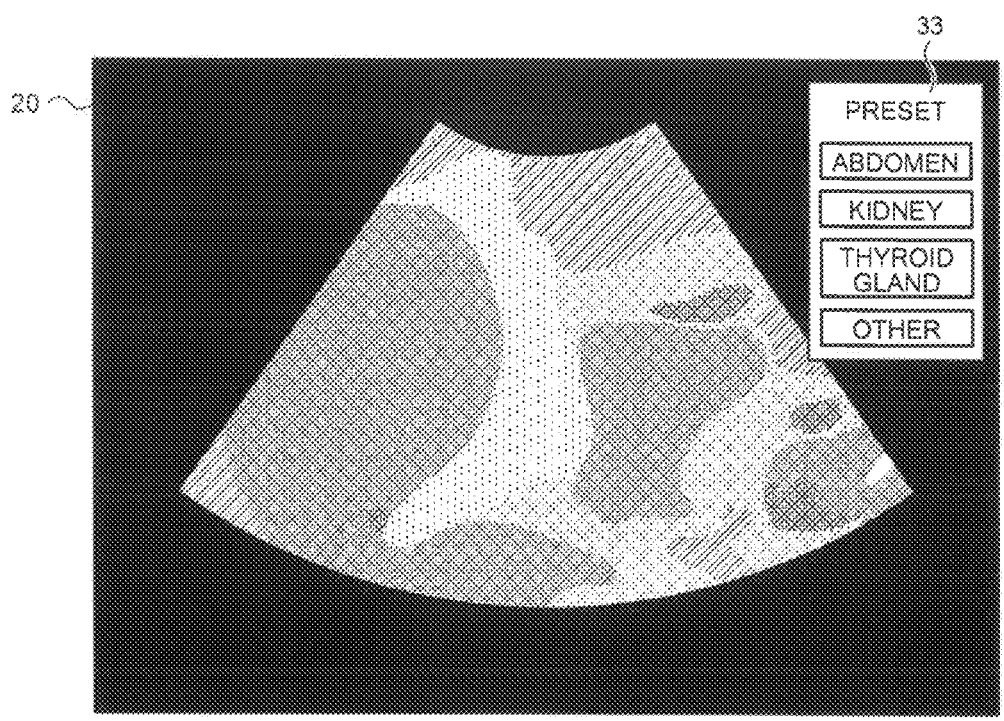

Still further, for example, the input unit 2b receives the operation of touching the area 23. Here, according to the setting information of FIG. 3, the data corresponding to the area 23 has "preset" in the menu information for live display of 2D imaging. Thus, for this case, the display control unit 17a displays a preset menu 33 in the display area 20, as illustrated in FIG. 7. The preset menu 33 is used by the operator to select a diagnosis target site.

Figure 8:
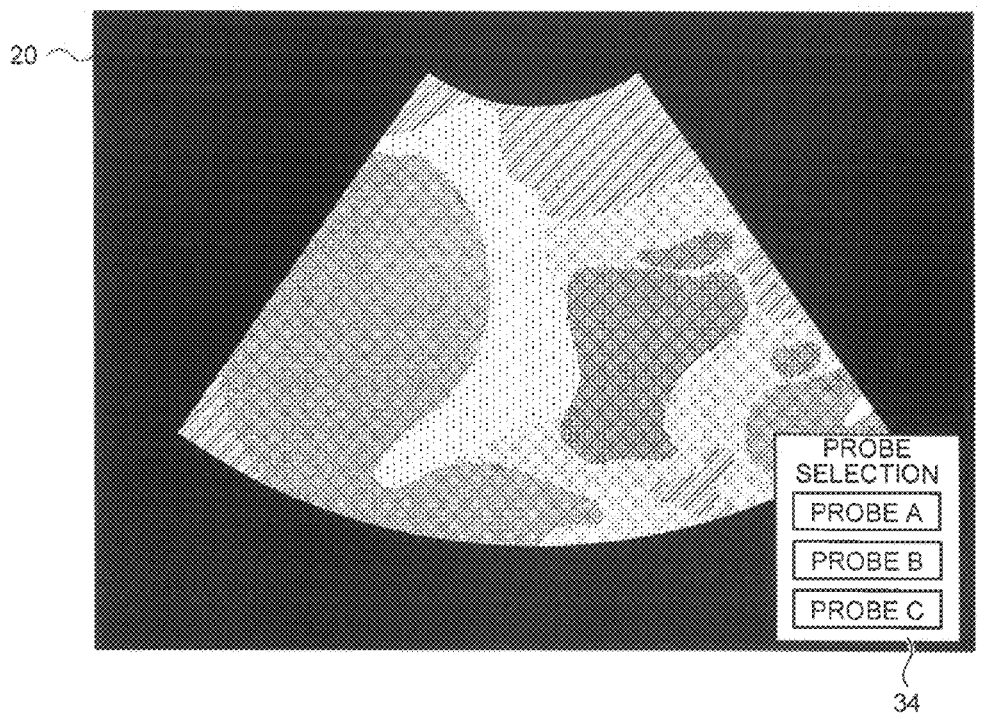

Still further, for example, the input unit 2b receives the operation of touching the area 24. Here, according to the setting information of FIG. 3, the data corresponding to the area 24 has "probe selection" in the menu information for live display of 2D imaging. Thus, for this case, the display control unit 17a displays a probe selection menu 34 in the display area 20, as illustrated in FIG. 8. The probe selection menu 34 is used by the operator to select the ultrasonic probe 1 that is to be adopted for the ultrasonic imaging from among the multiple ultrasonic probes.

Figure 9:
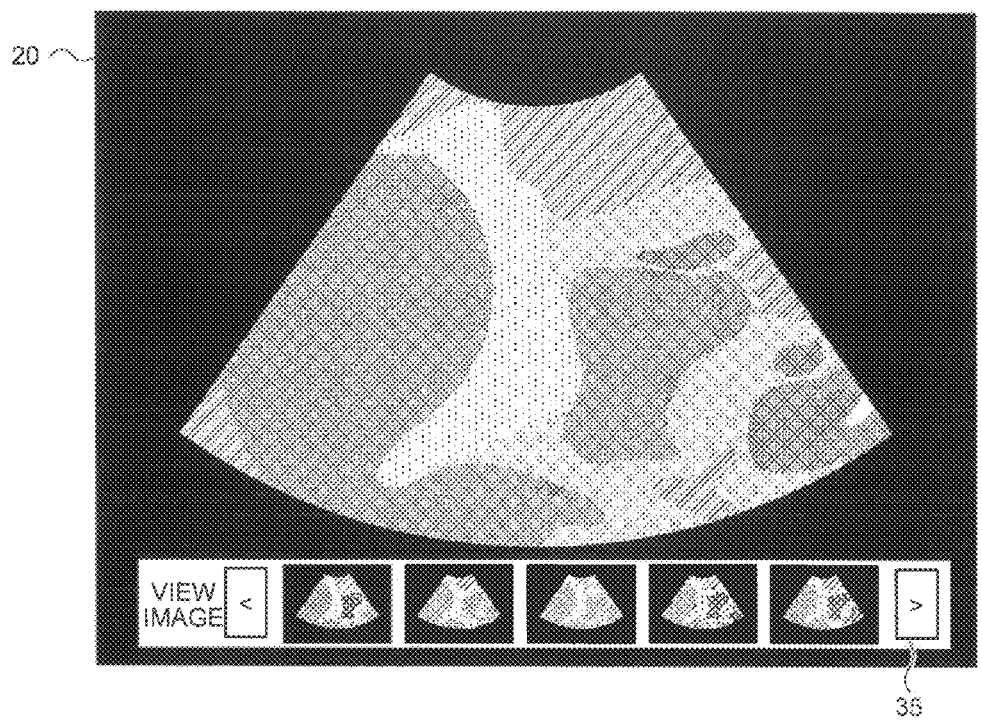

Still further, for example, the input unit 2b receives the operation of touching the area 25. According to the setting information of FIG. 3, the data corresponding to the area 25 has "image viewing" in the menu information for live display of 2D imaging. Thus, for this case, the display control unit 17a displays an image viewing menu 35 in the display area 20, as illustrated in FIG. 9. The image viewing menu 35 is used by the operator to select an image that is to be displayed in the display area from among the previously taken ultrasonic images of the same subject. For example, the previously taken ultrasonic images are displayed in thumb-nailed form on the image viewing menu 35 so that the operator can select any one of the ultrasonic images that are displayed.

If, for example, freeze display is selected as the display mode, the display control unit 17a displays a menu in the display area 20, based on what is indicated in the 2D menu information for freeze display, according to the setting information stored in the setting information storage unit 18a. More specifically, the display control unit 17a may display a measurement menu for receiving selection of a specific measurement item in the display area 20, in accordance with the input received by the input unit 2b.

Figure 10:
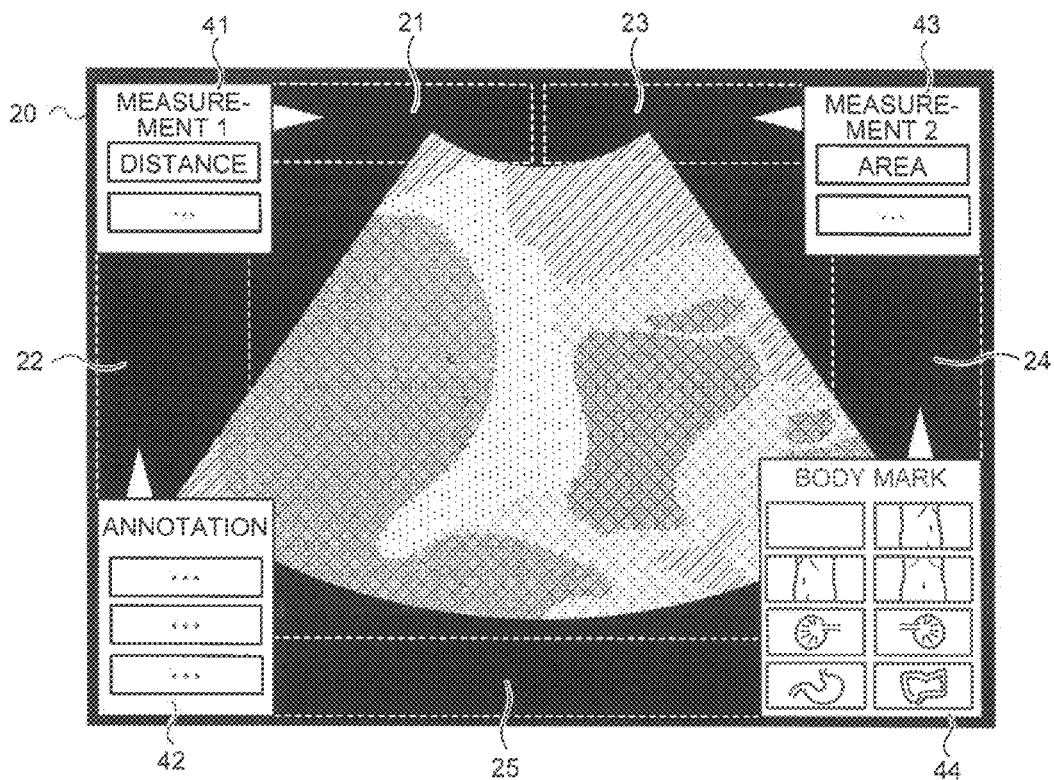

For example, the input unit 2b receives the operation of touching the area 21. According to the setting information of FIG. 3, the data corresponding to the area 21 has "measurement 1" in the menu information for freeze display of 2D imaging. Thus, for this case, the display control unit 17a displays in the display area 20, for example, a measurement menu 41 for measuring any distance in the ultrasonic image, as illustrated in FIG. 10.

Furthermore, the input unit 2b receives, for example, the operation of touching the area 22. Here, according to the setting information of FIG. 3, the data corresponding to the area 22 has "annotation" in the menu information for freeze display of 2D imaging. Thus, for this case, the display control unit 17a displays in the display area 20 an annotation menu 42 for attaching various kinds of information on the diagnosis, such as a type of tumor developed in the imaged site, to the ultrasonic image, as illustrated in FIG. 10.

Still further, the input unit 2b receives the operation of touching the area 23. Here, according to the setting information of FIG. 3, the data corresponding to the area 23 has "measurement 2" in the menu information for freeze display of the 2D imaging. Thus, for this case, the display control unit 17a displays, for example, a measurement menu 43 for measuring the size of any region included in the ultrasonic image in the display area 20, as illustrated in FIG. 10.

Still further, for example, the input unit 2b receives the operation of touching the area 24. Here, according to the setting information of FIG. 3, the data corresponding to the area 24 has "body mark" in the menu information for freeze display of the 2D imaging. Thus, for this case, the display control unit 17a displays in the display area 20 a body mark menu 44 for attaching a body mark to the ultrasonic image to show the position or orientation of the ultrasonic probe 1 placed on the subject, as illustrated in FIG. 10.

As discussed above, because the display control unit 17a changes a menu displayed in the display area in accordance with the display mode, a suitable menu can be displayed in accordance with the display mode when, for example, the menus used by the operator vary depending on the display mode of the ultrasonic image.

The display control unit 17a is configured, for example, to display a menu that is likely to be manipulated while the ultrasonic image is being examined, as illustrated in FIGS. 6 to 10, so as not to interfere with the examination of the ultrasonic image displayed in the display area 20. In other words, the display control unit 17a displays any menu that is likely to be manipulated while the ultrasonic image is being examined in such a manner that the area of the ultrasonic image that is hidden behind the menu is minimized in the display area 20.

In addition, after displaying a menu in correspondence with the position designating operation conducted by the operator, the display control unit 17a may perform control so that the displayed menu disappears from the display area after a predetermined period of time. In such a case, the display control unit 17a may further perform control so that the menu would not disappear after the predetermined period of time when an operation of requesting fixed menu display is received from the operator. In this manner, the operability of the menu display can be improved.

In FIG. 2, the menu processing control unit 17b controls all the units of the apparatus main body 10 in accordance with the menus under the control of the display control unit 17a. For example, the menu processing control unit 17b controls the later-explained transmission/reception control unit 17d in accordance with the input on the transmission/reception menu displayed in the display area 20. In addition, for example, the menu processing control unit 17b controls the later-described measuring unit 17e in accordance with the input on the measurement menu 41 or 43 displayed in the display area 20.

The transmission/reception control unit 17d controls the transmission and reception of the ultrasonic wave. This transmission/reception control unit 17d performs control, based on the input on the transmission/reception menu, under the control of the menu processing control unit 17b in such a manner as to start or stop the transmission and reception of the ultrasonic wave. More specifically, the transmission/reception control unit 17d controls the transmitting unit 11 and the receiving unit 12 of the apparatus main body 10 to stop or start the transmission and reception of the ultrasonic wave.

The measuring unit 17e performs measurements onto the ultrasonic image for certain measurement items. This measuring unit 17e performs control for the selected measurement item in accordance with the input on the measurement menu 41 or 43 under the control of the menu processing control unit 17b. For example, if input is made on the measurement menu 41, the measuring unit 17e executes the process of measuring a certain distance in the ultrasonic image. Furthermore, if input is made on the measurement menu 43, the measuring unit 17e executes the process of measuring the size of a certain region included in the ultrasonic image.

The measurements performed by the measuring unit 17e are not limited to the above. For example, the measuring unit 17e may perform measurements of the bloodstream speed in a Doppler image, the ratio of the bloodstream speeds during constriction and expansion, and the weight of a fetus estimated from the length of the spine and the size of the head at the examination.

The setting information changing unit 17c changes the association of the area information and the menu information in the setting information stored in the setting information storage unit 18a. The setting information changing unit 17c also changes the area position information and the area size information included in the setting information.

Figure 11:
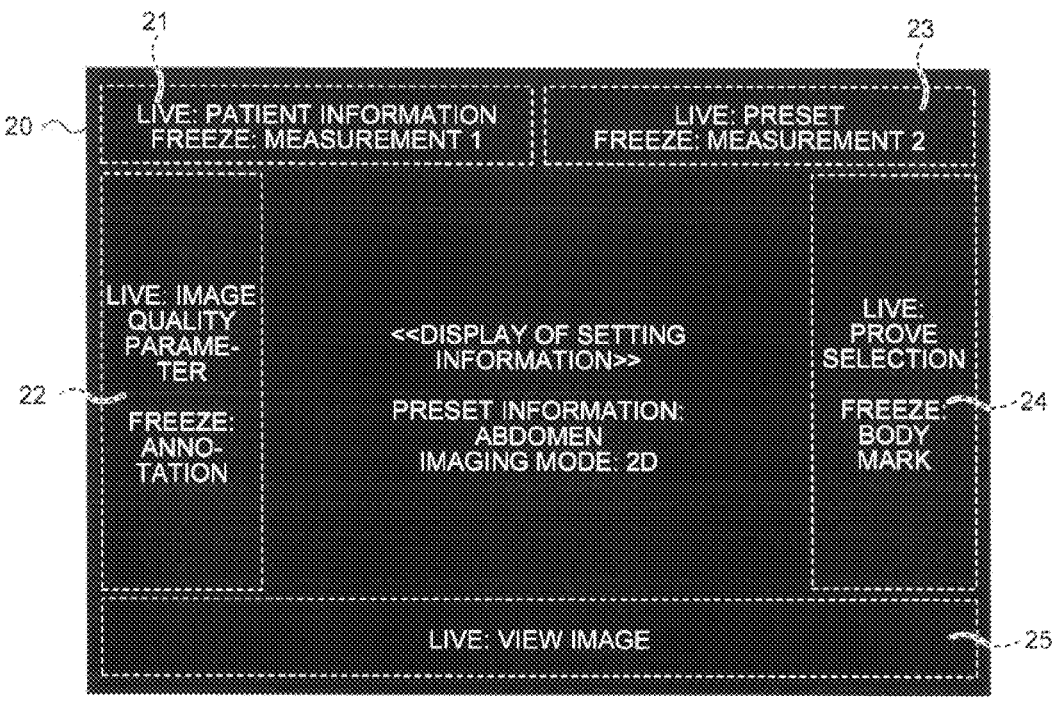
FIG. 11 is a diagram of an example layout of menus determined by a setting information changing unit according to the first embodiment.

For example, the setting information changing unit 17c displays in the display unit 2a the information indicating the layout of the menus in the display area, in response to a request from the operator. FIG. 11 is a diagram for showing an example of the menu layout displayed by the setting information changing unit 17c according to the first embodiment. As illustrated in FIG. 11 the setting information changing unit 17c displays, for example, the areas laid out in the display area 20 in broken lines, in accordance with the area information included in the setting information stored in the setting information storage unit 18a. The setting information changing unit 17c also displays, for each area, a live display menu and a freeze display menu that are brought into correspondence with each area. The setting information changing unit 17c changes the display illustrated in FIG. 11, for each site entered in the preset information and each imaging mode.

More specifically, the setting information changing unit 17c receives an operation of changing the association of the area and the menu from the operator, for the area displayed by the display unit 2a. For example, the setting information changing unit 17c receives an operation of rewriting information of the menu displayed in the area indicated in broken lines in the display area 20, as the operation of changing the association of the area and the menu. In accordance with the received operation, the setting information changing unit 17c changes the association of the area information and the menu information in the setting information stored in the setting information storage unit 18a.

Moreover, the setting information changing unit 17c receives from the operator the operation of changing the positions of the areas displayed in the display unit 2a. For example, the setting information changing unit 17c receives the operation of moving the areas shown in the broken lines in the display area 20, as the operation of changing the positions of the areas. Then, the setting information changing unit 17c changes the area position information that is included in the area information stored in the setting information storage unit 18a, in accordance with the received operation.

The setting information changing unit 17c also receives the operation of changing the sizes of the areas displayed on the display unit 2a from the operator. For example, the setting information changing unit 17c receives, as the operation of changing the sizes of the areas, the operation of enlarging or reducing any area indicated in broken lines in the display area 20. Then, the setting information changing unit 17c changes the area size information included in the area information stored in the setting information storage unit 18a, in accordance with the received operation.

Moreover, the setting information changing unit 17c receives the operation of changing the number of areas displayed on the display unit 2a from the operator. For example, the setting information changing unit 17c receives, as the operation of changing the number of areas, the operation of deleting any area indicated in broken lines in the display area 20 or the operation of adding an area indicated in broken lines in the display area 20. Then, the setting information changing unit 17c deletes the data of the deleted area and adds the data of the added area with respect to the area information stored in the setting information storage unit 18a, in accordance with the received operation.

Here, as indicated in FIG. 11, the information on the areas and menus that is displayed in the display area 20 has been explained. On the other hand, for example, the setting information indicated in FIG. 3 may be displayed in the form of a list in the display area 20. In this manner, the operator can make more modifications to the setting information at a time.

Figure 12:
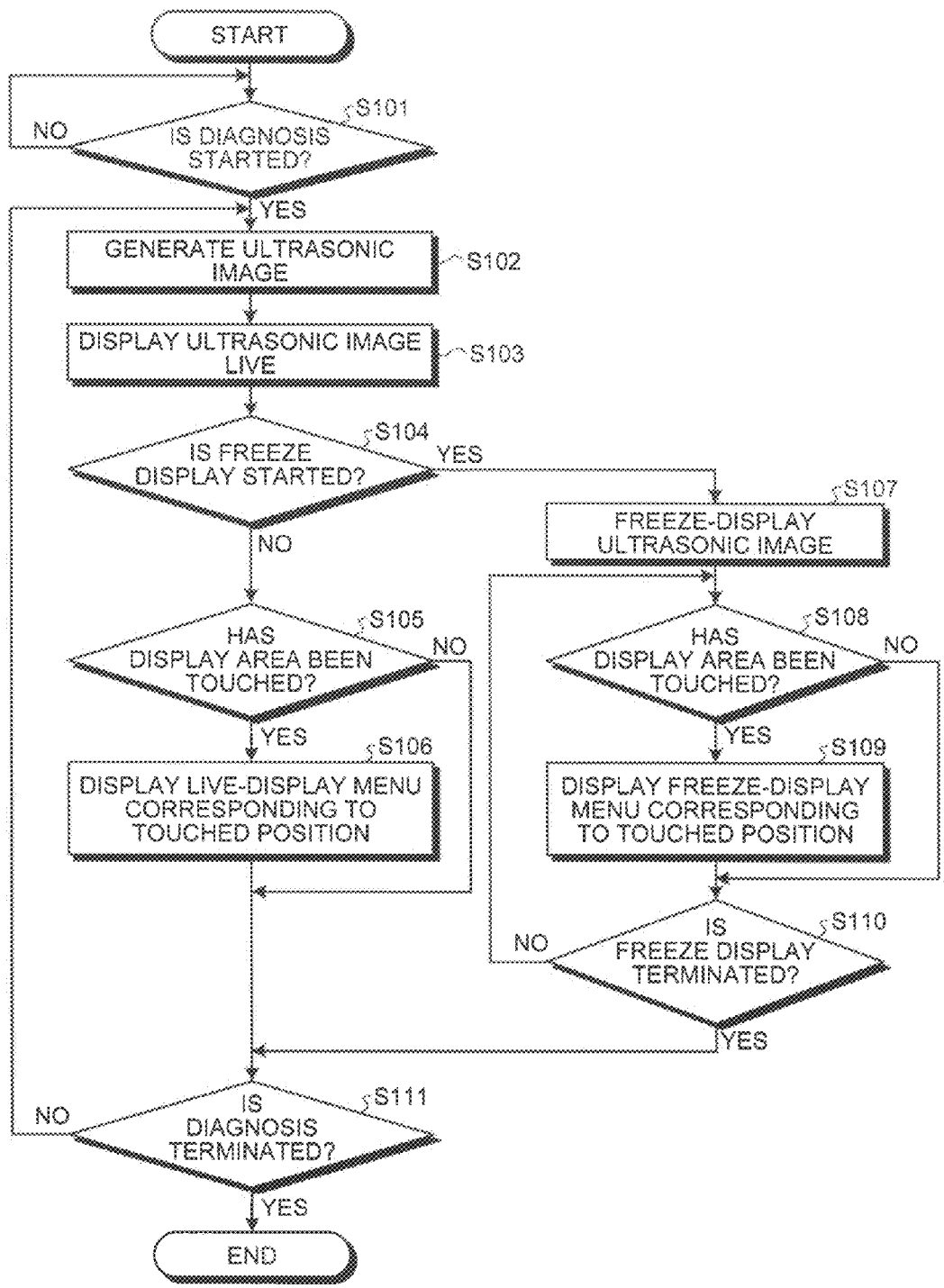
FIG. 12 is a flowchart for showing the process procedure of displaying a menu on the diagnostic ultrasonic apparatus according to the first embodiment.

Next, the procedure of the menu displaying process executed by the diagnostic ultrasonic apparatus according to the first embodiment is explained. FIG. 12 is a flowchart of the procedure of the menu displaying process executed on the diagnostic ultrasonic apparatus according to the first embodiment.

As indicated in FIG. 12, in the diagnostic ultrasonic apparatus according to the first embodiment, when the operator starts the diagnosis (yes at step S101), the apparatus main body 10 generates an ultrasonic image in accordance with a reflection wave signal received by the ultrasonic probe 1 (step S102).

In addition, the display control unit 17a displays the ultrasonic image generated by the apparatus main body 10 live on the display unit 2a (step S103). If the operator does not instruct to start the freeze display (no at step S104), the display control unit 17a continues to display the ultrasonic image live.

Then, when the operator touches the display area while the ultrasonic image is being displayed live (yes at step S105), the display control unit 17a displays the live display menu corresponding to the touched position (step S106). If the operator does not touch the display area (no at step S105), the display control unit 17a continues to generate and live-display the ultrasonic image without displaying any menu until the operator terminates the diagnosis (no at step S111).

In addition, if the operator instructs to start the freeze display during the live display of the ultrasonic image (yes at step S104), the display control unit 17a freeze-displays the ultrasonic image generated by the apparatus main body 10 onto the display unit 2a (step S107).

Then, if the operator touches the display area during the freeze display of the ultrasonic image (yes at step S108), the display control unit 17a displays the freeze display menu corresponding to the touched position on the display area (step S109). If the operator does not touch the display area (no at step S108), the display control unit 17a continues to freeze-display the ultrasonic image without displaying any menu, until the operator issues instructions to terminate the freeze display (no at step S110).

Furthermore, when the operator issues instructions to terminate the freeze-display (yes at step S110), the display control unit 17a returns to the display mode of displaying the ultrasonic image live, and performs generation and live display of the ultrasonic image until the operator terminates the diagnosis (no at step S111).

Then, when the operator terminates the diagnosis while the ultrasonic image is being displayed live (yes at step S111), the display control unit 17a terminates the live display of the ultrasonic image.

As discussed above, according to the first embodiment, the display unit 2a includes a display area to display an ultrasonic image. In addition, the input unit 2b receives a position input operation for inputting a position in the display area included in the display unit 2a. Then, when the input unit 2b receives the position input operation, the display control unit 17a displays a menu in relation to the ultrasonic image in the display area. Thus, according to the first embodiment, a menu is displayed only when it is necessary for the operator, and therefore the display area of the monitor can be effectively used during the examination of the ultrasonic image.

Furthermore, according to the first embodiment, the display unit 2a and the input unit 2b are realized by a touch panel. Thus, according to the first embodiment, a necessary menu is displayed when an area predetermined in the display area of the touch panel is touched, and thus the operator can perceptively perform operations.

In addition, according to the first embodiment, the setting information storage unit 18a stores therein setting information in which area information indicating an area provided in the display area of the display unit 2a and menu information indicating a type of menu are associated with each other. Then, based on the setting information stored in the setting information storage unit 18a, the display control unit 17a displays in the display area a menu that is brought into correspondence with the area including the position input through the position input operation. Hence, according to the first embodiment, a menu that is predetermined for each area provided in the display area can be displayed.

In addition, according to the first embodiment, the menu information stored in the setting information storage unit 18a includes information on the live display menu that is used during the live display of an ultrasonic image and the freeze display menu that is used during the freeze display of an ultrasonic image. Then, depending on the live display or freeze display of the ultrasonic image, the display control unit 17a determines whether the live display menu or the freeze display menu is to be displayed. Hence, according to the first embodiment, a suitable menu can be displayed in accordance with the display mode of the ultrasonic image when the menu used by the operator varies in accordance with the display mode.

In addition, according to the first embodiment, the setting information changing unit 17c changes the association of the area information and the menu information in the setting information stored in the setting information storage unit 18a. Thus, according to the first embodiment, the operator is allowed to freely change a menu, for each area, that is displayed when an area provided in the display area is designated.

Further, according to the first embodiment, the area information stored in the setting information storage unit 18a includes area position information that indicates an area provided in the display area. Then, the setting information changing unit 17c changes the area position information included in the area information. Thus, according to the first embodiment, the operator is allowed to freely change the position of the area provided in the display area.

In addition, according to the first embodiment, the area information stored in the setting information storage unit 18a includes area size information that indicates the size of an area provided in the display area. Then, the setting information changing unit 17c changes the area size information included in the area information. Hence, according to the first embodiment, the operator is allowed to freely change the size of the area provided in the display area.

According to the first embodiment, the structure in which areas laid out in the display area are not displayed has been explained. On the other hand, for example, the display control unit 17a may display the areas in a transparent color or in frames in the display area. In this manner, the operator can easily recognize the range in which the areas are laid out in the display area. In this case, for example, information necessary for the display of the areas, such as information on the hue and shade of the transparent color, is added as display information to the setting information illustrated in FIG. 3. Then, the display control unit 17a displays the areas in the display area by use of the display information included in the setting information. In addition, the setting information changing unit 17c may be configured to change the display information in response to the operator's request. In this manner, the operator is allowed to freely change the display style of the areas displayed in the display area.

In addition, according to the first embodiment, the structure in which the input unit 2b of the touch panel 2 receives from the operator the operation of touching any position in the display area of the display unit 2a as the position input operation has been discussed. On the other hand, for example, the operating unit 3 may receive the position input operation from the operator by way of a mouse, a keyboard, buttons, panel switches, trackballs, and the like. In such a case, the operating unit 3 may receive the operator's operation of clicking the mouse on the display area, and send the screen position information indicating the clicked position to the display control unit 17a. In this manner, even if, for example, the input unit 2b of the touch panel 2 develops trouble and becomes unusable, the operator can still have a menu displayed on the display area.

Furthermore, according to the first embodiment, the structure in which a menu is displayed when the position designation operation is received from the operator has been explained. For example, the display control unit 17a may be configured to switch between the display mode explained in the first embodiment and the conventional display mode of displaying the menus and the ultrasonic image together, in response to the operator's request. In this manner, the manner of displaying menus can be suitably changed in accordance with the type of diagnosis and the operator's preference.

Furthermore, according to the first embodiment, for example, the display of menus that are generally used for the operator of the diagnostic ultrasonic apparatus to perform operations in relation to the ultrasonic image, such as the patient information menu 31, the image quality parameter menu 32, the preset menu 33, the probe selection menu 34, and the image viewing menu 35, has been explained. On the other hand, when an operation different from any of the generally used menus that have been discussed in the first embodiment is received from the operator, the display control unit 17a may be configured to display in the display area a menu specially used by a service person or the like who performs maintenance of the display diagnostic ultrasonic apparatus. The specially used menu may be an initial setting menu that is used for initial settings when the diagnostic ultrasonic apparatus is newly installed in a hospital or the like and a setting change menu that is used by a service person to change the system settings. In such a situation, for example, the display control unit 17a is configured to display these menus in the display area when the operator touches a certain area laid out in the display area of the display unit 2a for a predetermined length of time (e.g., 5 seconds) or longer.

In addition, according to the first embodiment, the structure in which multiple areas are displayed in the display area of the display unit 2a and operations in relation to these areas are received so that various menus are displayed has been discussed. In contrast, a sensor may be provided in the frame of the monitor that has a displaying function only so that when the sensor detects that the operator touches any position of the frame, the display control unit 17a can display a menu corresponding to the touched position. In such a situation, for example, when the position of a frame in the upper part of the monitor is touched, the display control unit 17a displays the patient information menu 31 in the display area, while when the position of a frame in the right part of the monitor is touched, the display control unit 17a displays the probe selection menu 34 in the display area.

In addition, the diagnostic ultrasonic apparatus has been discussed in the first embodiment, but the exemplary embodiments are not limited thereto. For example, the menu displaying function explained in the first embodiment may be implemented in other diagnostic imaging apparatus such as an X-ray diagnostic apparatus, an X-ray computed tomography (CT) apparatus, a magnetic resonance imaging (MRI) apparatus.

Figure 13:
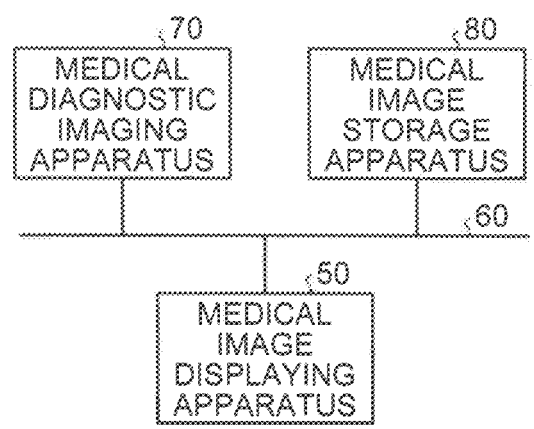
FIG. 13 is a diagram for showing a medical image management system including a medical image displaying apparatus according to the second embodiment.

Next, as the second embodiment, the medical image displaying apparatus is explained. FIG. 13 is a diagram of a medical image management system including a medical image displaying apparatus 50 according to the second embodiment. As illustrated in FIG. 13, for example, the medical image displaying apparatus 50 is connected to a medical diagnostic imaging apparatus 70 and a medical image storage apparatus 80 by way of a network 60 in a communicable manner.

The medical diagnostic imaging apparatus 70 collects medical images of the subject. This medical diagnostic imaging apparatus 70 may be a diagnostic ultrasonic apparatus, a magnetic resonance imaging apparatus, or an X-ray computed tomography (CT) apparatus. The medical diagnostic imaging apparatus 70 generates a medical image in the imaging format, for example, based on the digital imaging and communications in medicine (DICOM) standard.

The medical image storage apparatus 80 stores therein the medical images collected by the medical diagnostic imaging apparatus 70. For example, the medical image storage apparatus 80 stores therein the medical images generated by the medical diagnostic imaging apparatus 70 in the imaging format based on the DICOM standard.

The medical image displaying apparatus 50 obtains a medical image from the medical diagnostic imaging apparatus 70 or the medical image storage apparatus 80, and displays the obtained medical image. The medical image displaying apparatus 50 is, for example, an image viewer or a workstation.

Figure 14:
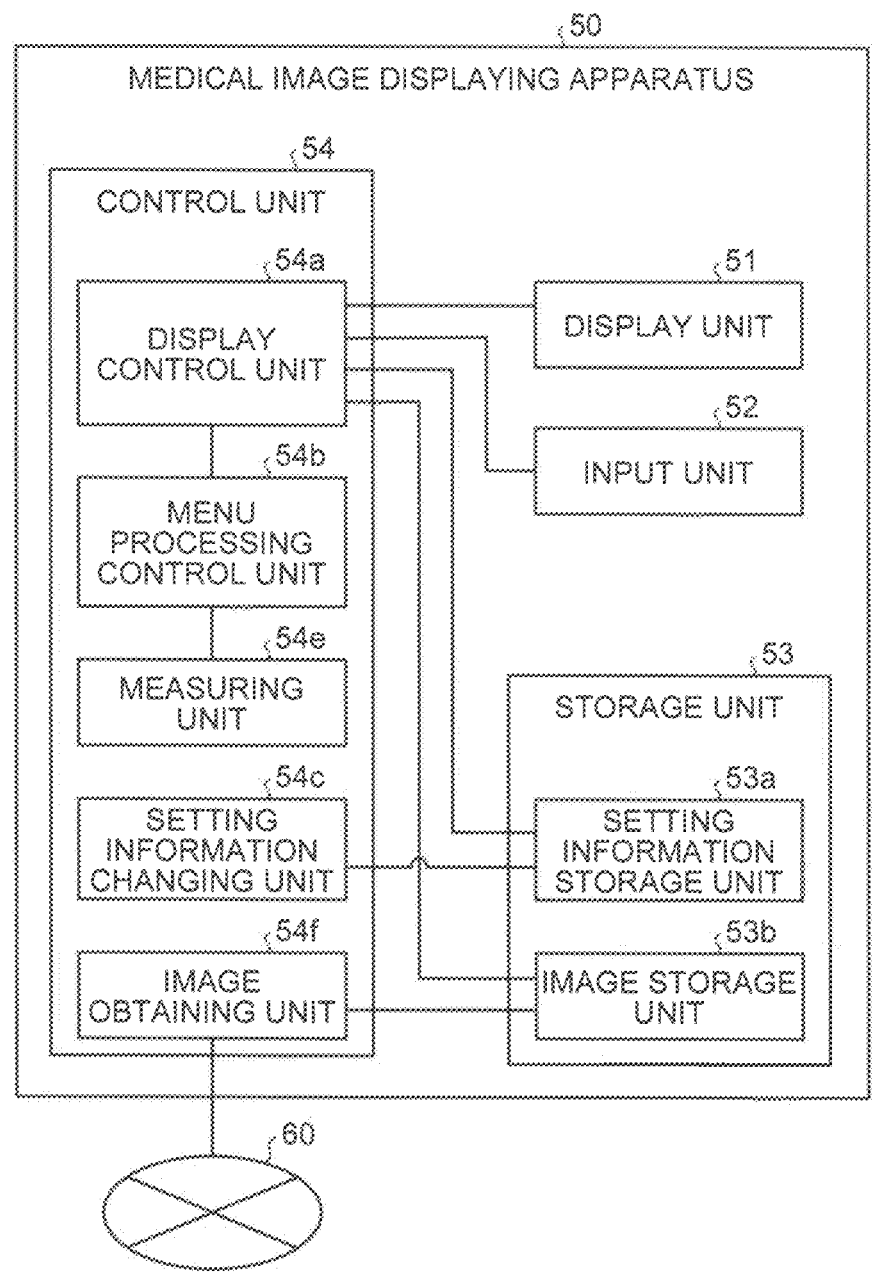
FIG. 14 is a block diagram for showing the structure of the medical image displaying apparatus according to the second embodiment.

FIG. 14 is a block diagram for showing the structure of the medical image displaying apparatus 50 according to the second embodiment. As illustrated in FIG. 14, the medical image displaying apparatus 50 according to the second embodiment includes, for example, a display unit 51, an input unit 52, a storage unit 53, and a control unit 54.

The display unit 51 includes a display area to display a medical image. The display unit 51 is, for example, a liquid crystal monitor or a cathode ray tube (CRT) monitor. For example, the display unit 51 displays various medical images and various menus in relation to the medical images, under the control of a later-described display control unit 54a.

The input unit 52 receives input of various kinds of information from the operator. The input unit 52 may be a mouse or a keyboard. For example, the input unit 52 receives a position input operation with which a position in the display area of the display unit 51 is input. As a specific example, the input unit 52 receives, as a position input operation, an operation of clicking any position in the display area of the display unit 51 with the mouse from the operator. In addition, when the position in the display area is clicked by the operator, the input unit 52 sends screen position information that indicates the clicked position to the display control unit 54a.

The display unit 51 and the input unit 52 may be provided by the touch panel.

The storage unit 53 stores therein various types of medical information. The storage unit 53 may be a hard disk drive or a semiconductor memory. For example, the storage unit 53 includes a setting information storage unit 53a and an image storage unit 53b.

The setting information storage unit 53a stores therein, in the same manner as the setting information storage unit 18a described in the first embodiment, setting information in which area information indicating an area provided in the display area of the display unit 51 and menu information indicating a type of menu are associated with each other. According to the second embodiment, the area information indicates an area provided in the display area of the display unit 51. Furthermore, according to the second embodiment, the menu information indicates a type of menu in relation to medical images.

For example, according to the second embodiment, information on the menu for display of moving images and information on the menu for display of still images are provided as the menu information. Here, the menu for moving image display is used when a medical moving image is being displayed. Moreover, the menu for still image display is used when a medical still image is being displayed.

The image storage unit 53b stores therein various medical images obtained from the medical diagnostic imaging apparatus 70 or the medical image storage apparatus 80.

The control unit 54 includes the display control unit 54a, a menu processing control unit 54b, a setting information changing unit 54c, a measuring unit 54e, and an image obtaining unit 54f.

The image obtaining unit 54f obtains a medical image from the medical diagnostic imaging apparatus 70 or the medical image storage apparatus 80 by way of the network 60. For example, the image obtaining unit 54f sends, in response to the operator's request, a medical image obtaining request to the medical diagnostic imaging apparatus 70 or the medical image storage apparatus 80, and receives a medical image in response to this obtaining request. Then, the image obtaining unit 54f stores the received medical image in the image storage unit 53b.

The display control unit 54a displays various medical images and various menus in relation to the medical images onto the display unit 51. For example, the display control unit 54a receives an instruction of the moving image display or the still image display of a medical image from the operator, and performs the moving image display or the still image display of the medical image designated by the operator onto the display area of the display unit 51, in accordance with the received instruction.

Furthermore, the display control unit 54a displays a menu in relation to the medical images in the display area of the display unit 51 when the input unit 52 receives a position input operation. The display control unit 54a displays different menus in the display area, in response to the input received by the input unit 52. More specifically, the display control unit 54a displays a menu that is brought into correspondence with the area that includes the position input through the position input operation in the display area of the display unit 51, based on the setting information stored in the setting information storage unit 53a.

Furthermore, the display control unit 54a displays the moving image display menu or the still image display menu, depending on whether the medical image is displayed as a moving image or a still image. More specifically, when the medical image is displayed as a moving image, the display control unit 54a displays the menu in the display area 20, based on the information determined as the menu information for moving image display in the setting information stored in the setting information storage unit 53a. For example, the display control unit 54a displays, if the medical image is displayed as a moving image, a menu for receiving an instruction of slow-motion playback or frame-by-frame playback of the moving image, in the display area 20.

On the other hand, if the medical image is displayed as a still image, the display control unit 54a displays a menu in the display area 20, based on the information determined in the menu information for still image display in the setting information stored in the setting information storage unit 53a. For example, the display control unit 54a displays a measurement menu for receiving selection of a specific measurement item in the display area, in response to the input received by the input unit 2b. Otherwise, the display control unit 54a displays menus such as "patient information", "image quality parameter", and "image viewing" in the display area, in the same manner as the first embodiment.

The control of the menu display performed by the display control unit 54a is the same as the control of the menu display performed by the display control unit 17a according to the first embodiment, and thus detailed explanations are omitted here.

The menu processing control unit 54b controls the units of the apparatus main body 10 so that processes are executed in correspondence with individual menus under the control of the display control unit 54a. For example, the menu processing control unit 54b controls the later-described measuring unit 54e, in accordance with the input on the measurement menu 41 or 43 displayed in the display area 20.

The measuring unit 54e performs measurement onto the medical image for a specific measurement item. This measuring unit 54e performs measurement in relation to the selected measurement item under the control of the menu processing control unit 54b, based on the input on the measurement menu. For example, in response to the input on the measurement menu, the measuring unit 54e performs a process of measuring a certain distance in the ultrasonic image or a process of measuring the size of a certain area included in the ultrasonic image.

The setting information changing unit 54c changes the association between the area information and the menu information in the setting information stored in the setting information storage unit 53a. Furthermore, the setting information changing unit 54c changes the area position information included in the setting information and the area size information included in the setting information. The function of the setting information changing unit 54c is the same as that of the setting information changing unit 17c explained in the first embodiment, and thus detailed explanations are omitted here.

As described above, the medical image displaying apparatus 50 according to the second embodiment includes the image obtaining unit 54f, the image storage unit 53b, the display unit 51, the input unit 52, and the display control unit 54a. The image obtaining unit 54f obtains medical images. The image storage unit 53b stores therein the medical images.

The display unit 51 includes a display area to display the medical images. The input unit 52 receives input in relation to the display area of the display unit 51. Then, the display control unit 54a displays different menus in the display area of the display unit 51 in accordance with the input received by the input unit 52. Thus, according to the second embodiment, a menu is displayed only when it is necessary for the operator, and thus the display area of the display unit 51 can be effectively used during the examination of the medical image.

As discussed above, according to the first and second embodiments, the display area of the display unit can be effectively used during the examination of the medical image.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An apparatus, comprising:
a display that includes a display area in which a medical image is displayed;
an input circuit that receives a single input designating a position within the display area, wherein the designated position does not correspond to a selectable and movable icon displayed in the display area;
a processor that displays, in the display area, a menu of a plurality of different menus corresponding to a plurality of respective different areas provided in the display area, wherein a type of the displayed menu is determined by the designated position of the single input received by the input circuit; and
a setting information memory that stores therein setting information including area information indicating an area provided in the display area, and menu information indicating a type of the menu, the area information and the menu information being stored in association with each other, wherein
the processor
changes, according to an instruction from an operator, the association of the area information and the menu information in the setting information stored in the setting information memory, and
identifies an area including the designated position from among the plurality of different areas provided in the display area, and displays, as said menu, a menu corresponding to the identified area based on the setting information.

2. The apparatus according to claim 1, wherein the display and the input circuit are implemented by a touch panel; and
the input circuit receives a touch input of the designated position in the display area on the touch panel.

3. The apparatus according to claim 1, wherein:
the setting information further includes area position information and area size information;
the processor further changes the area position information or the area size information; and
the processor identifies the area including the designated position based on the area position information and the area size information.

4. The apparatus according to claim 1, wherein
the menu information includes information on a first menu that is used when the medical image is being displayed as a moving image and on a second menu that is used when the medical image is being displayed as a still image; and
the processor determines which one of the first menu and the second menu should be displayed, depending on whether the medical image is being displayed as the moving image or as the still image.

5. The apparatus according to claim 1, wherein the processor
performs a measurement on the medical image with respect to measurement items,
displays a measurement menu in the display area and receives selection of one of the measurement items, in accordance with the input received by the input circuit; and
performs the measurement with respect to the measurement item that is selected, in accordance with the input on the measurement menu.

6. A diagnostic ultrasonic apparatus, comprising:
a transmission/reception controller that controls transmission/reception of an ultrasonic wave;
an image generating processor that generates an ultrasonic image based on an echo signal of the ultrasonic wave;
a display that includes a display area in which the ultrasonic image is displayed;
an input circuit that receives a single input designating a position within the display area, wherein the designated position does not correspond to a selectable and movable icon displayed in the display area;
a processor that displays, in the display area, a menu of a plurality of different menus corresponding to a plurality of respective different areas provided in the display area, wherein a type of the displayed menu is determined by the designated position of the single input received by the input circuit; and
a setting information memory that stores therein setting information including area information indicating an area provided in the display area, and menu information indicating a type of the menu, the area information and the menu information being stored in association with each other, wherein
the processor
changes, according to an instruction from an operator, the association of the area information and the menu information in the setting information stored in the setting information memory, and
identifies an area including the designated position from among the plurality of different areas provided in the display area, and displays, as said menu, a menu corresponding to the identified area based on the setting information.

7. The diagnostic ultrasonic apparatus according to claim 6, wherein the display and the input circuit are implemented by a touch panel; and
the input circuit receives a touch input of the designated position in the display area on the touch panel.

8. The diagnostic ultrasonic apparatus according to claim 6, wherein:
the setting information further includes area position information and area size information;
the processor further changes the area position information or the area size information; and
the processor identifies an area including the designated position based on the area position information and the area size information.

9. The diagnostic ultrasonic apparatus according to claim 6, wherein:
the menu information includes information on a first menu that is used when the medical image is being displayed as a moving image and on a second menu that is used when the medical image is being displayed as a still image; and
the processor determines which one of the first menu and the second menu should be displayed, depending on whether the medical image is being displayed as the moving image or displayed as the still image.

10. The diagnostic ultrasonic apparatus according to claim 6, wherein:
the processor displays a transmission/reception menu in the display area to receive stop or start of transmission/reception of the ultrasonic wave in accordance with the input received by the input circuit; and
the transmission/reception controller performs control in accordance with input on the transmission/reception menu so that the transmission/reception of the ultrasonic wave stops or starts.

11. The diagnostic ultrasonic apparatus according to claim 6, wherein the processor
performs a measurement on the medical image with respect to measurement items,
displays a measurement menu in the display area and receives selection of one of the measurement items, in accordance with the input received by the input circuit; and
performs the measurement with respect to the measurement item that is selected, in accordance with the input on the measurement menu.

12. A medical image displaying apparatus, comprising:
a processor that obtains a medical image;
an image memory that stores therein the medical image;
a display that includes a display area in which the medical image is displayed;
an input circuit that receives a single input designating a position within the display area, wherein the designated position does not correspond to a selectable and movable icon displayed in the display area, wherein the processor displays, in the display area, a menu of a plurality of different menus corresponding to a plurality of respective different areas provided in the display area, wherein a type of the displayed menu is determined by the designated position of the single input received by the input circuit;
a setting information memory that stores therein setting information including area information indicating an area provided in the display area, and menu information indicating a type of the menu, the area information and the menu information being stored in association with each other, wherein
the processor
changes, according to an instruction from an operator, the association of the area information and the menu information in the setting information stored in the setting information memory, and
identifies an area including the designated position from among the plurality of different areas provided in the display area, and displays, as said menu, a menu corresponding to the identified area based on the setting information.

13. The diagnostic imaging apparatus according to claim 12, wherein the display and the input circuit are implemented by a touch panel; and the input circuit receives a touch input of the designated position in the display area on the touch panel.

14. The medical image displaying apparatus according to claim 12, wherein the setting information further includes area position information and area size information;

the processor further changes the area position information or the area size information; and the processor identifies the area including the designated position based on the area position information and the area size information.

15. The medical image displaying apparatus according to claim 12, wherein the menu information includes information on a first menu that is used when the medical image is being displayed as a moving image and information on a second menu that is used when the medical image is being displayed as a still image; and the processor determines which one of the first menu and the second menu is to be displayed, depending on whether the medical image is being displayed as the moving image or the still image.

16. The medical image displaying apparatus according to claim 12, wherein the processor performs a measurement on the medical image with respect to measurement items, displays a measurement menu in the display area and receives selection of one of the measurement items, in accordance with the input received by the input circuit; and performs the measurement with respect to the measurement item that is selected, in accordance with the input on the measurement menu.

17. An apparatus, comprising:

a monitor that includes a screen in which a medical image is displayed;

an input circuit that receives a single input designating a position from positions each fixed relative to the screen;

a processor that displays, in the screen, a menu of a plurality of different menus corresponding to a plurality of respective different areas provided in the display area, wherein a type of the displayed menu is determined by the designated position of the single input received by the input circuit;

a setting information memory that stores therein setting information including area information indicating an area provided in the display area, and menu information indicating a type of the menu, the area information and the menu information being stored in association with each other, wherein the processor changes, according to an instruction from an operator, the association of the area information and the menu information in the setting information stored in the setting information storage, and identifies an area including the designated position from among the plurality of different areas provided in the display area, and displays, as said menu, a menu corresponding to the identified area based on the setting information.

18. An apparatus, comprising:

a display that includes a display area in which a medical image is displayed;

an input circuit that receives input designating a position within the display area;

a processor that displays, in the display area, a menu of a plurality of different menus corresponding to a plurality of respective different areas provided in the display area, wherein a type of the displayed menu is determined by the designated position of the input received by the input circuit and depending on whether the medical image is being displayed as a moving image or as a still image;

a setting information memory that stores therein setting information including area information indicating an area provided in the display area, and menu information indicating a type of the menu, the area information and the menu information being stored in association with each other, wherein the processor changes, according to an instruction from an operator, the association of the area information and the menu information in the setting information stored in the setting information storage, and identifies an area including the designated position from among the plurality of different areas provided in the display area, and displays, as said menu, a menu corresponding to the identified area based on the setting information.

19. The apparatus according to claim 18, wherein the input is a single input designating the position within the display area; and the type of the displayed menu is determined by the designated position of the single input received by the input circuit.

* * * * *